United States Patent [19]

Doyle

[11] Patent Number: 5,065,025
[45] Date of Patent: Nov. 12, 1991

[54] GAS SAMPLE ANALYSIS PROVIDED BY LIGHT PIPE RADIATION STRUCTURE

[75] Inventor: Walter M. Doyle, Laguna Beach, Calif.

[73] Assignee: Axiom Analytical, Inc., Laguna Beach, Calif.

[21] Appl. No.: 487,619

[22] Filed: Mar. 2, 1990

[51] Int. Cl.⁵ .............................................. G01N 21/61
[52] U.S. Cl. ................................... 250/343; 250/573; 356/437
[58] Field of Search .................... 250/343, 428, 432 R, 250/435, 437, 438, 573; 356/440, 437; 350/96.32

[56] References Cited

U.S. PATENT DOCUMENTS

| | | |
|---|---|---|
| 3,861,809 | 1/1975 | Hall ..................................... 250/343 |
| 4,420,690 | 12/1983 | Kuehl ................................... 250/343 |
| 4,588,893 | 5/1986 | Vidrine et al. ....................... 250/428 |
| 4,692,622 | 9/1987 | Taniguchi et al. ................... 250/343 |

FOREIGN PATENT DOCUMENTS 3340505 5/1985 Fed. Rep. of Germany ...... 356/246

OTHER PUBLICATIONS

Hanse, Philip L., Infrared Analysis, Inc., "Specialists in the Measurement of Gases", (company brochure).

Primary Examiner—Carolyn E. Fields
Assistant Examiner—James E. Beyer
Attorney, Agent, or Firm—Thomas J. Plante

[57] ABSTRACT

A gas cell for use in spectrometric analysis is disclosed, in which a series of pipes provide both the gas chamber and a light guide for infrared radiation which passes through the gas to accomplish the analysis. The light pipe is designed to provide a maximum radiation throughput of a collimated radiation beam. The same pipe provides laminar gas flow into and out of the gas cell. In other words, the gas when moving is not obstructed or restricted by changes in the cross-sectional area of its passageway.

20 Claims, 8 Drawing Sheets

GAS SAMPLE ANALYSIS PROVIDED BY LIGHT PIPE RADIATION STRUCTURE

BACKGROUND OF THE INVENTION

This invention relates to gas cells used in spectroscopic analysis. A gas cell confines the gas which is being analyzed; and radiation (infrared) is caused to pass through the confined gas.

Long path infrared cells are widely used for the spectroscopic analysis of gases. Typical applications include the analysis of gases involved in chemical manufacturing processes, monitoring of emissions from combustion sources ranging from automobile engines to toxic waste incinerators, and the detection of hazardous gases in the industrial environment. The most commonly used cells are called "White" cells. The design of these cells minimizes internal gas volume by using multiple radiation passes back and forth through a gas-containing chamber. FIG. 1 shows a typical White cell chamber and optical system.

Such cells have certain practical limitations which limit their utility for many industrial applications. First, the cell diameter is quite large compared to any fittings which might be used for pumping gas into and out of it. Thus, despite the relatively small volume, the total amount of flushing gas required to clean out a sample can be quite large. Second, the alignment of the mirrors in a White cell is very critical, making such a cell difficult to use in harsh industrial applications and, in particular, in applications requiring high temperatures or pressures.

The present invention is intended to provide a gas cell which: (a) avoids the need for mirror adjustments inside the cell; (b) tolerates changes in heat or pressure without affecting alignment; and (c) eliminates gas flow problems in filling and emptying the cell.

STATEMENT OF THE INVENTION

The present invention uses a single structure to provide both a gas cell and a light pipe. In other words, a tube-like structure is used to confine both the gas being analyzed and a collimated radiation beam passing through the gas.

The light pipe radiation transmission may incorporate the features disclosed in common inventor, common assignee application Ser. No. 07/487,601, filed Mar. 2, 1990. Those features are arranged to enhance radiation throughput, and to permit a lengthy radiation path without undue radiation loss. The long radiation path provides an equally long gas cell, in which gas may be either stationary or flowing during analysis.

The gas flow in the cell is essentially laminar, i.e., the gas passes into one end of the light pipe and exits from the other end of the light pipe, with substantially no restrictions of the area of its passageway.

The only mirrors needed in the light pipe gas cell are flat, direction-changing mirrors which reflect collimated radiation through a series of side-by-side pipes. A single long pipe may be used; but a group of parallel pipes provides a more compact structure.

DETAILED DESCRIPTION OF SPECIFIC EMBODIMENTS

Figure 1:
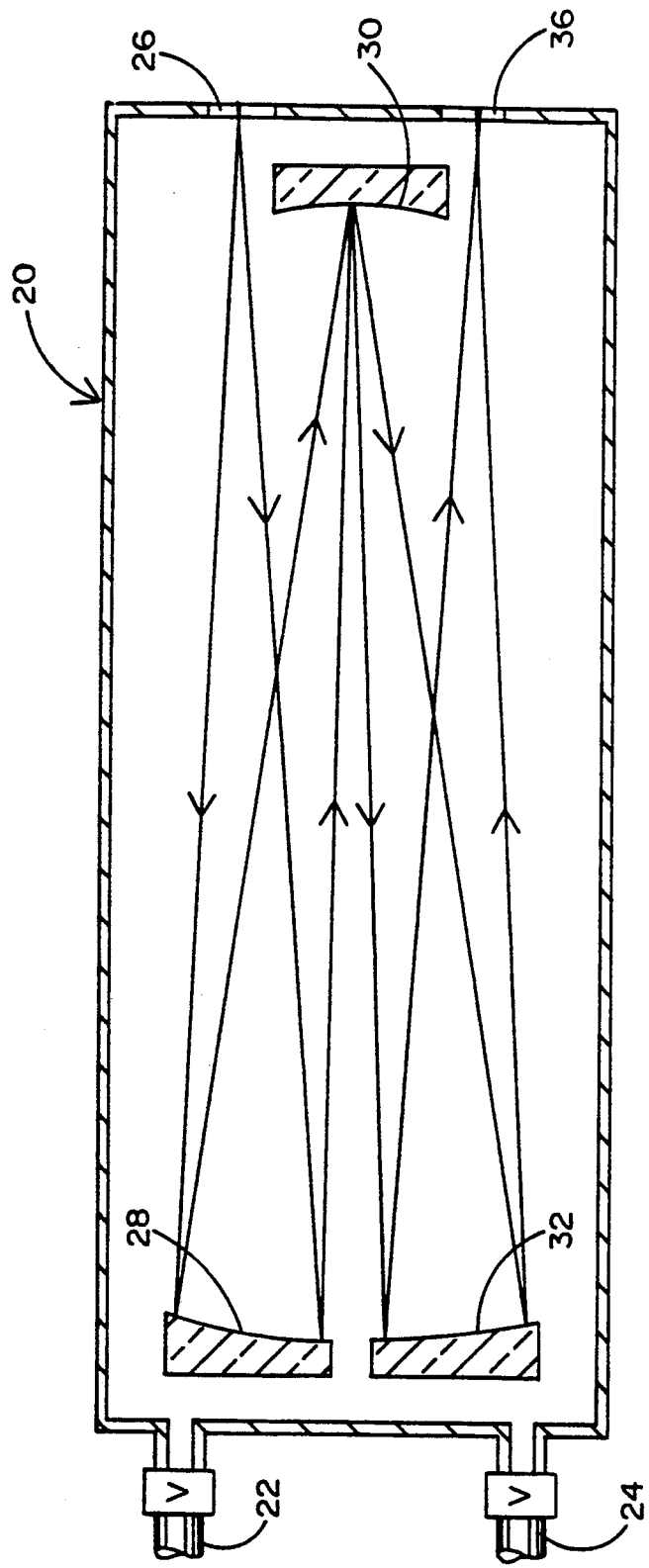
FIG. 1 shows schematically a prior art "White cell"

FIG. 1 shows a prior art "White Cell", used for gas analysis. A relatively large diameter chamber 20 has, at its left end, a gas inlet opening 22 controlled by a suitable valve, and a gas outlet opening 24 controlled by a suitable valve. Radiation enters through a window 26 at the right end of the chamber, is reflected inside the chamber by a plurality of mirrors 28, 30, and 32, and exits through a window 36 at the right end of the chamber. The radiation from the source is focused at entrance 26, refocused at mirror 30, and again refocused at the exit 36. The radiation in the cell usually strikes each mirror several times, in order to provide the desired radiation path length.

The gas sample to be analyzed is pumped in through inlet valve 22. It is trapped in the chamber during analysis; and is thereafter evacuated through outlet valve 24 by means of a vacuum pump.

The remaining figures disclose the fundamentally different gas cell of the present invention. A series of tubes provide a long path for collimated radiation, which is used to analyze the gas sample present in those tubes. A given sample of gas may be retained during analysis, and then removed. Or a continuous gas flow may occur during analysis.

Figure 2:
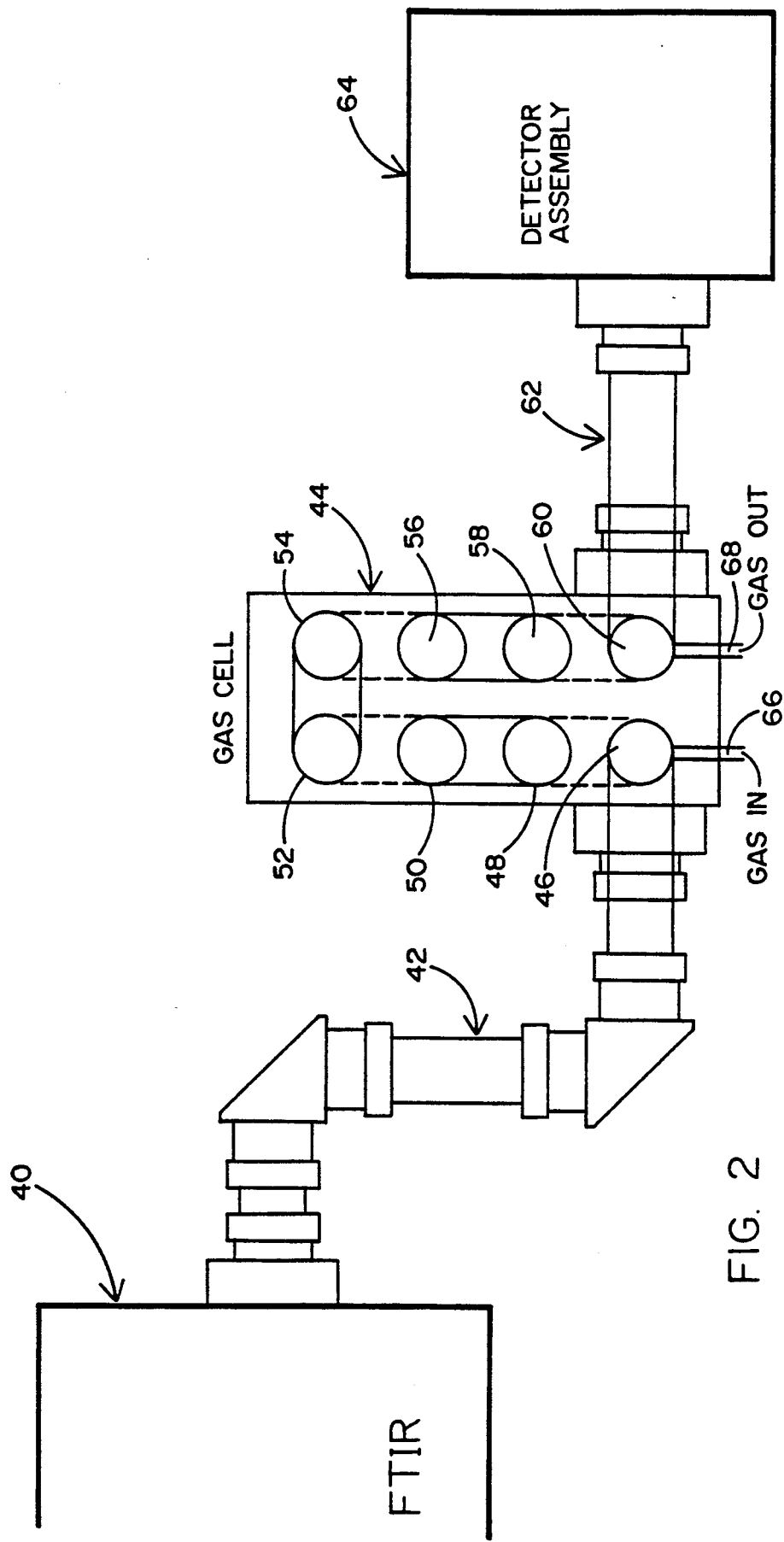
FIG. 2 shows, from the bottom, a spectrometer system incorporating the gas cell/light pipe arrangement of the present invention.

FIG. 2 shows diagrammatically a spectrometer system incorporating applicant's novel gas cell. An FTIR spectrometer unit 40 directs pre-sample collimated radiation through an optical light pipe assembly 42 into a gas cell assembly 44. The collimated radiation enters the gas cell through a transparent window, which keeps gas from entering the spectrometer portion of the system. In the gas cell, which is seen from the bottom, the radiation beam passes upwardly through tubes 46, 50, 54, and 58, and downwardly through tubes 48, 52, 56 and 60. From tube 60, the radiation beam is directed by a light pipe 62 to a detector assembly 64.

A gas inlet 66 permits gas to flow into the bottom of tube 46, and to follow the same path as the radiation. A gas outlet 68 is located at the bottom of tube 60. A transparent window is provided to prevent gas from entering the detector portion of the system.

Figure 3:
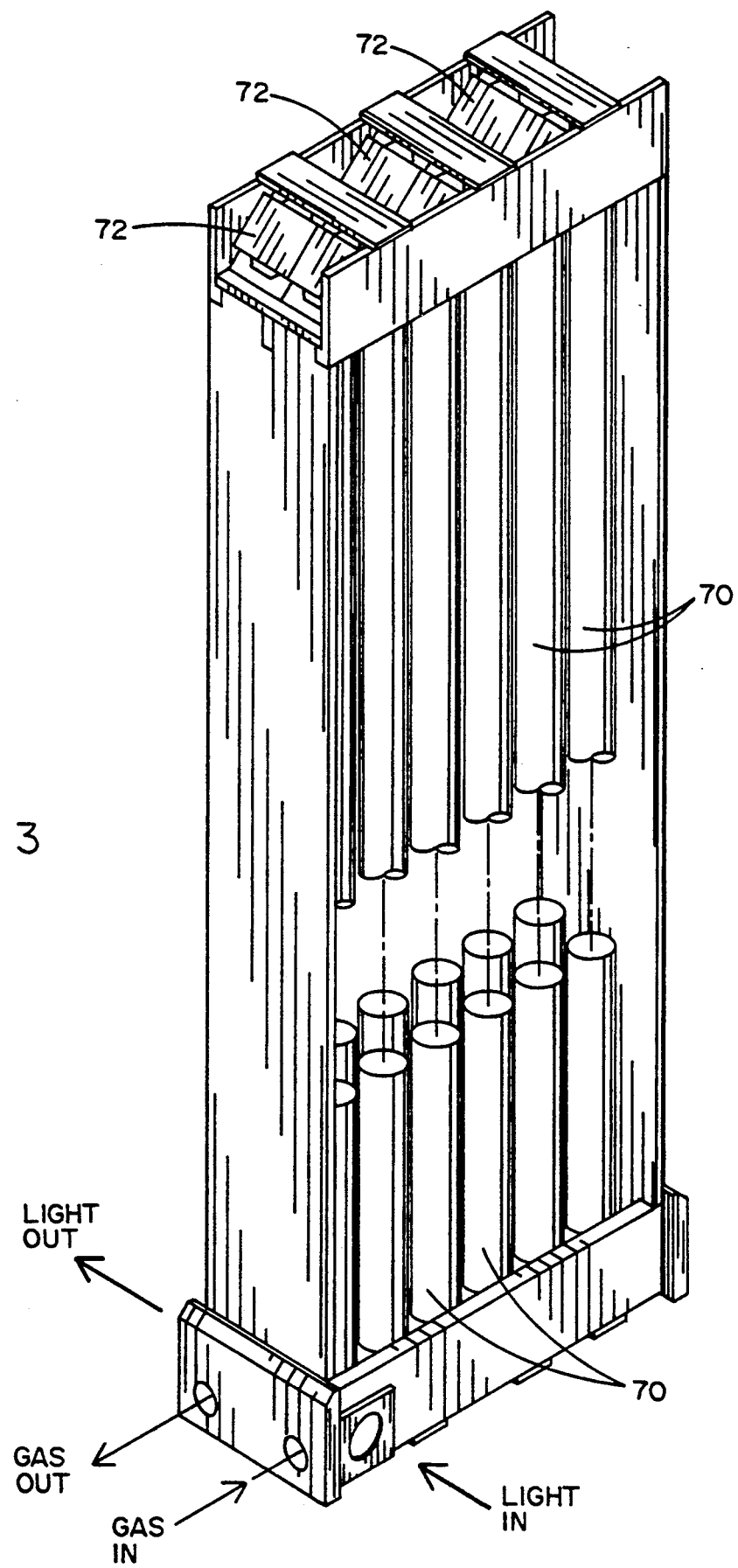
FIG. 3 is an isometric view of a structure containing a plurality of parallel gas cell/light pipe tubes secured in a unitary assembly.

FIG. 3 shows isometrically a gas cell/light pipe assembly having twelve parallel tubes 70. Each pair of adjacent tubes 70 is optically "bridged" at top and bottom by a "roof-top" mirror unit 72 which effectively conserves radiation throughput, while reversing the radiation path. The multiple tube arrangement provides a long radiation path and large volume gas cell in a relatively compact space.

Figure 4:
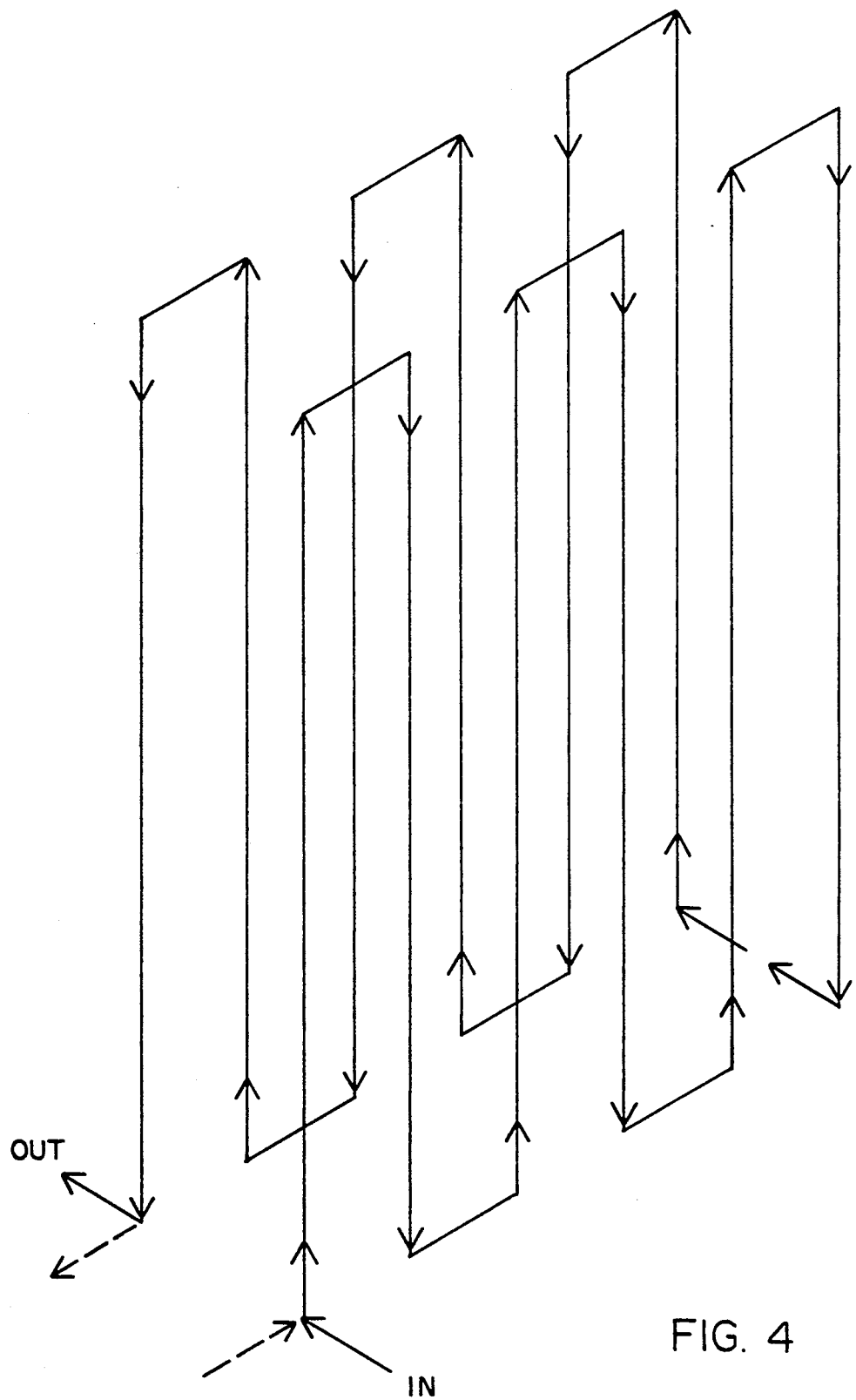
FIG. 4 shows the paths of the radiation and gas in the tube assembly of FIG. 3.

FIG. 4 uses arrows to show the radiation path in the gas cell assembly of FIG. 3. The gas flow follows the same path, entering and leaving as indicated by the dashed line arrows.

Figure 5:
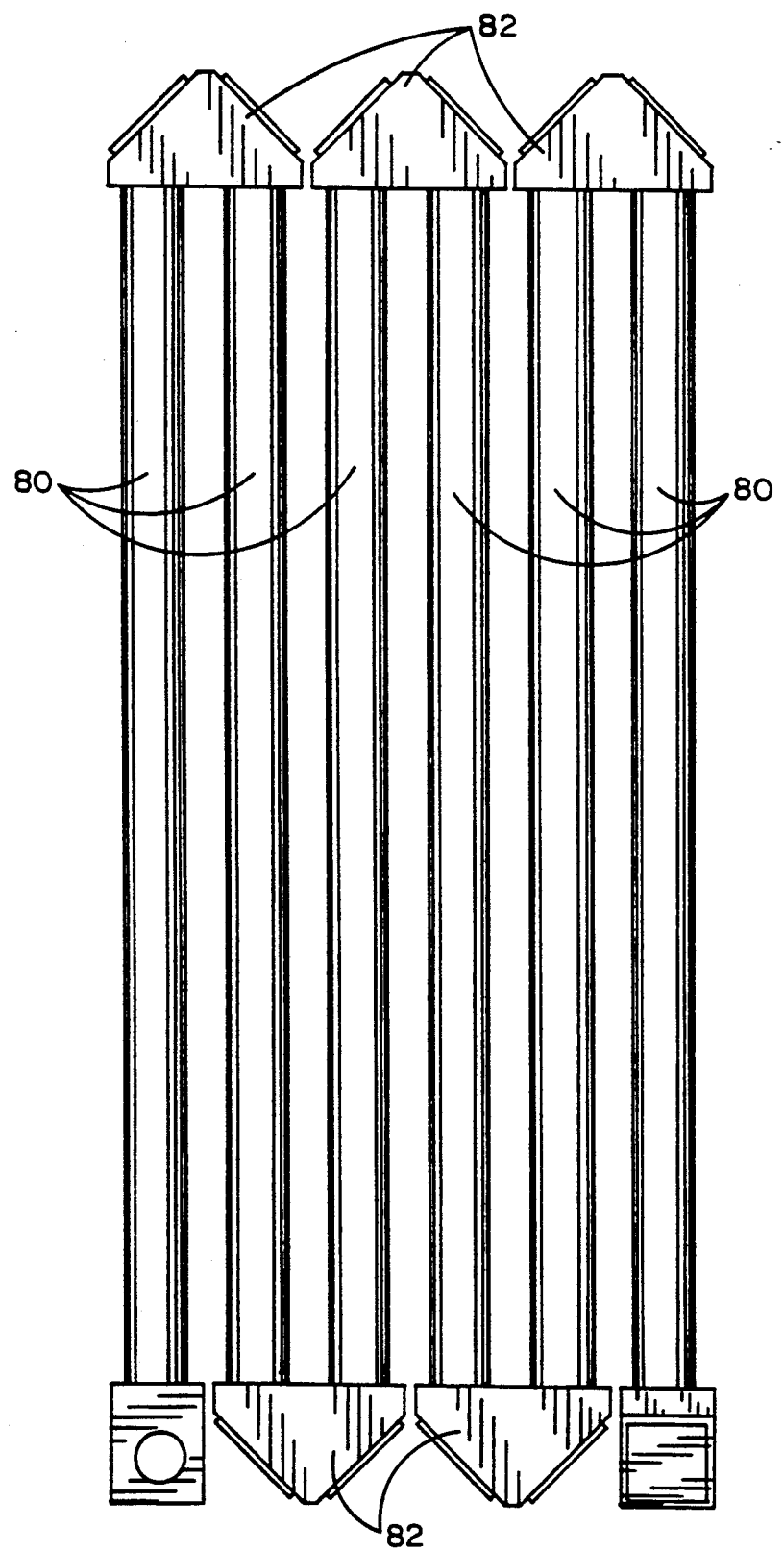
FIG. 5 shows a side view of six tubes having roof-top radiation reflecting units interconnecting (bridging) adjacent tubes.
Figure 6:
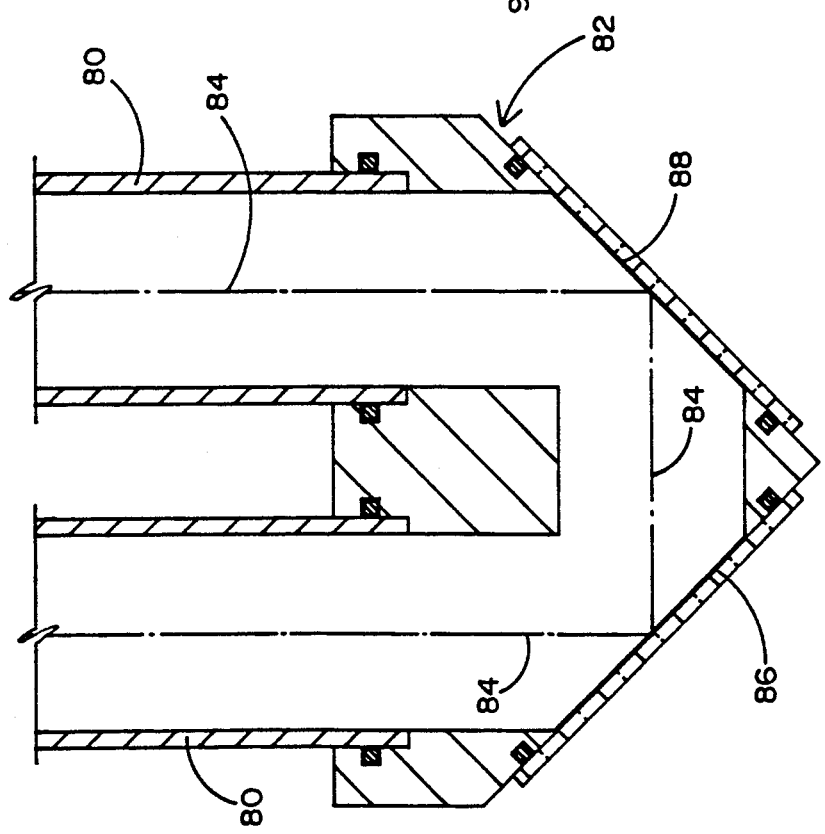
FIG. 6 is a cross-section through one of the roof-top reflecting units of FIG. 5.

FIG. 5 is a side view showing an air-cell/light-pipe assembly having six parallel tubes 80, and five "bridging" roof-top mirror units 82. FIG. 6 shows a cross-section of one of the roof-top mirror units 82. The dashed line 84 indicates the axis of the collimated radiation beam. If the beam travels downwardly in the left pipe 80, it is reflected first by a flat mirror 86, then by a flat mirror 88, and then travels upwardly in the right pipe 80.

Figure 7:
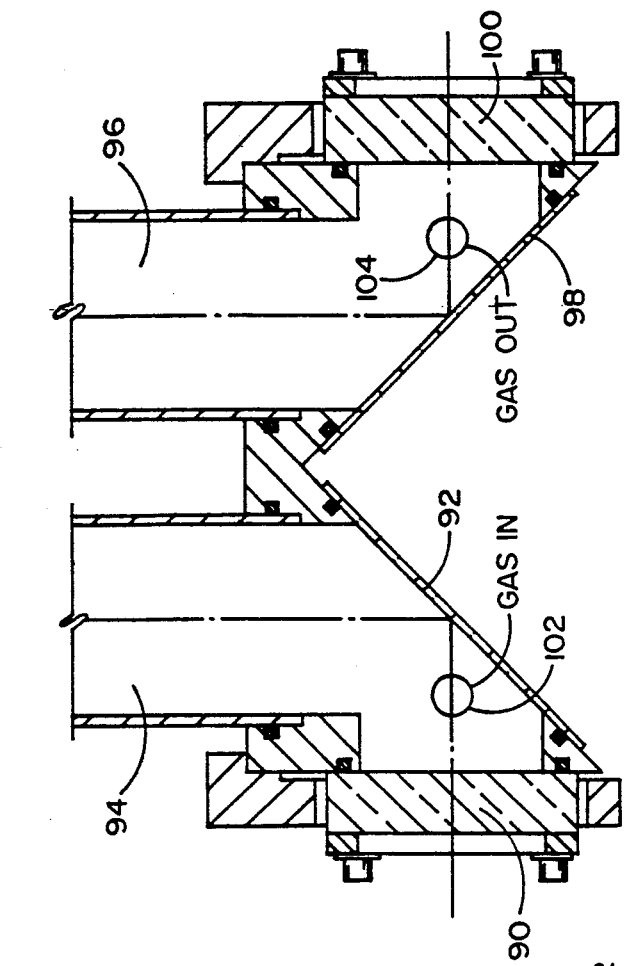
FIG. 7 is a cross-section through a fitting which provides the input and output ports for both the radiation and the gas.

FIG. 7 is a cross-section taken at the in/out fitting. Radiation from the spectrometer, entering from the left, passes through a window 90, which may be a potassium bromide (KBr) plate. The radiation is reflected by a flat mirror 92, and travels upwardly in the first tube 94. Radiation leaving the last tube 96 is reflected by a flat mirror 98, and travels to the right toward the detector through a KBr window 100. Gas enters at an inlet 102, and exits at an outlet 104.

As previously stated, the apparatus of the present application has several benefits as a gas cell. These benefits are made possible by the optical performance of the light pipe system disclosed in the related application Ser. No. 07/487,601.

Because of the long tubular gas cell volume, the shape of the cell is consistent with approximately laminar gas flow. In other words, the diameter of the cell volume is of the same order of magnitude as fittings used to connect it to the source of gas to be analyzed and to a pumping system used to exhaust previously analyzed gas.

With the White cell, it is necessary to use a gas volume equal to several times the cell volume to flush out a given sample. In contrast, with the new cell, approximately one cell volume of gas should suffice for the flushing, since the previous sample will simply flow on ahead of the flushing gas as an intact "plug", as it would through any gas transmission pipe.

In the preferred embodiment, the path is folded into a relatively compact form as shown in the drawings. All of the optical elements are either internally plated tubes or flat glass mirrors. They are inexpensive and easily replaced if they become contaminated. In addition, the cell length can be varied by adding or subtracting tube sections and rooftop mirror assemblies.

Compared to the White cell, the present invention has the following advantages:

(1) No optical adjustments are needed. The mirrors are simply mounted accurately relative to the axis of the light pipes.

(2) The cell can be heated or pressurized without affecting alignment.

(3) Since the new cell is in the form of a long narrow pipe, it can be used for the analysis of continuously flowing gas, in which case the essentially laminar flow will insure that no residual sample will be left in the cell to compromise subsequent measurements. This same characteristic allows the cell to be easily pumped out and refilled even when used for non-flowing samples.

The optical features disclosed in the related application Ser. No. 07/487,601 are necessary to provide the present gas cell invention. As stated in that application, a plurality of concepts are relevant to the successful use of light pipes for effective transmission of radiation:

(1) A nominally collimated beam is used, which has an area (cross-sectional) substantially equal to the area of the cylindrical passage in the light pipe (or pipes). The cylindrical passage is, of course, as reflective as possible, in order to minimize radiation absorption by the light pipe.

(2) The light pipe is preferably large in diameter, so as to minimize the number of ray reflections per unit of length. This may also be described as a way of permitting use of a longer gas cell/light pipe, because of practical limits on the length-to-diameter ratio of the light pipe.

(3) The nominally collimated radiation beam should have minimum, and uniform, angular divergence of the rays across the face of the beam. This divergence depends, in part, on the diameter of the detector. Use of a detector which is as small as possible minimizes angular ray divergence, and thus minimizes radiation loss in the light pipe.

(4) A surprising finding is that reflective metallic coating on the interior of the light pipe may provide better throughput with a material which does not have the highest reflectivity, but which has preferred values of "k" (the "imaginary" part of its index of refraction) and "n" (the "real" part of its index of refraction). A relatively high value of "k" and relatively low value of "n" will move the minimum point on the curve of reflectance-versus-angle to a larger grazing angle. This, in turn, makes it possible to take advantage of the rapid increase in reflectance that takes place as the ray angle approaches grazing incidence.

(5) If the detector diameter is small enough that the maximum divergence angle is smaller than the angle corresponding to the minimum of the reflectance curve (referred to in the preceding paragraph) an improved throughput efficiency can be attained.

As further stated in application Ser. No. 07/487,601, light guides, in the form of pipes having highly reflective internal surfaces, will transmit mid-infrared radiation. However, the conventional wisdom is that such light pipes are too lossy (highly absorbing) to be useful as general purpose transmission means for mid-infrared. This belief is based partly on experience and partly on theory. For example, workers designing GC/IR (gas chromatograph infrared) light pipes have noted that the transmitted signal level falls off rapidly with length to diameter ratios exceeding 100 or 200. Although various limited uses of light pipes have occurred, in the instances known to applicant, they have, as in U.S. Pat. No. 4,730,882, used a small diameter pipe, and focused the infrared radiation into the end of the light pipe. With such an arrangement, the radiation will cover a range of incidence angles from 90° (grazing) down to typically 70°. Applicant has discovered that light pipes may, in fact, be used quite successfully for reasonably long distance transmission of incoherent radiation, provided certain important principles are followed in designing such light pipes and the systems in which they are incorporated.

The interior walls of the light pipes, which also serve as gas tubes, have highly reflective surfaces, usually provided by a metallic coating. The diameter of the collimated radiation beam is large enough to fill the internal diameter of the light pipes. If the beam were perfectly collimated, i.e., coherent, or if the interior surfaces of the light pipes were 100% reflective, radiation loss would not be a problem. But the radiation (which is not coherent) has an angle of diversion which makes it impossible to have all rays traveling parallel to the light pipe walls; and 100% reflectivity (zero absorbance) is not obtainable. As a result, rays in the radiation beam will be reflected from the light pipe walls; and each reflection of a ray will cause a loss of throughput due to absorption of a small percentage of the ray intensity.

Figure 8:
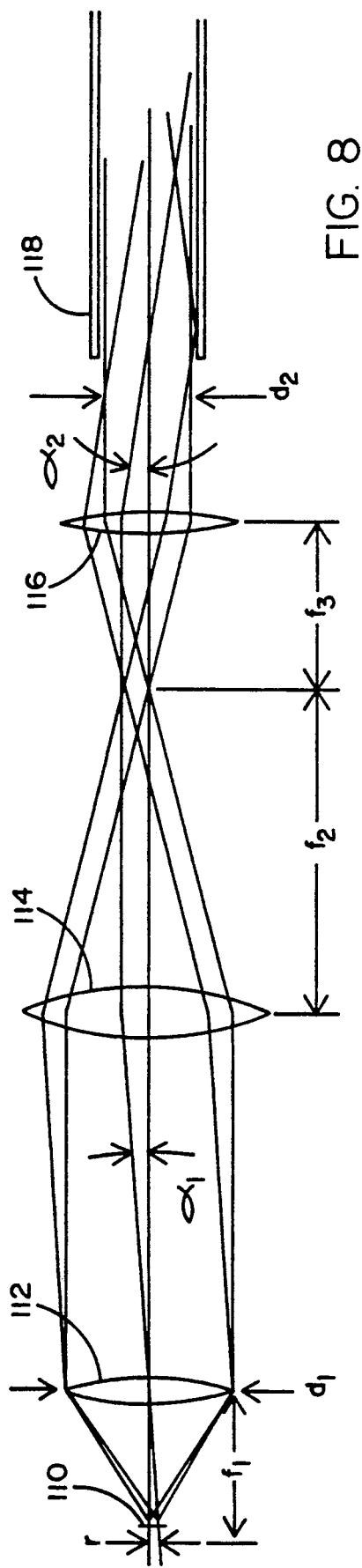
FIG. 8 and 9 are substantially identical to FIGS. 4 and 6, respectively, of the related application.

FIG. 8, which corresponds to FIG. 4 in the related application, is an optical diagram which illustrates the relationship between beam divergence and beam diameter for a constant throughput optical system. In the figure, lenses are shown as the optical elements, for the sake of simplicity. In a typical infrared system, parabolic mirrors are used rather than lenses. But the general conclusions apply to either arrangement, although the mirrors do cause some departure from ideal conditions (more complicated aberrations).

In discussing FIG. 8, it is assumed that the maximum throughput of the system is determined by the detector optics rather than by the interferometer or sampling system. This is most often the case when working at low spectral resolutions. Note that throughput is a measure of the total amount of optical power that can be transmitted by a system. It is equal to the area of the optical beam times the solid angle beam divergence (taken in a plane where the beam has a uniform intensity distribution).

In FIG. 8, r is the radius of the detector 110, $f_1$ is the focal length of the detector lens 112, and $d_1$ is the diameter of this lens. If the detector is located in the focal plane of the lens, the detector will "see" a bundle of radiation entering the lens which has a half angle divergence equal to alpha1, where $\tan alpha_1 = r/f_1$. For small angles, the solid angle beam divergence will equal $3.1416(r/f_1)^2$; and the throughput in the detector plane will be approximately $3.1416(alpha_1 d_1/2)^2$.

The second and third optical elements (lenses 114 and 116) of FIG. 8 constitute a beam condenser (or expander) intended to match the diameter of the detector's field of view to that of a light guide 118. Lens 114 has a focal length of $f_2$; and lens 116 has a focal length of $f_3$. Ideally the end of the light guide would be located in the plane indicated by diameter $d_2$, where there are both a minimum beam diameter and a uniform distribution of ray angles and positions. From the construction shown in FIG. 4, it can be seen that the following conditions apply:

$$d_2 = d_1(f_3/f_2) \text{ and } alpha_2 = alpha_1(f_2/f_3)$$

From this it can be seen that the throughput in plane $d_2$ will be the same as in the plane of detector lens 112, and that the divergence angle will be inversely proportional to the beam diameter $d_2$.

By using an appropriate beam condenser (or expander), the diameter of the beam can always be matched to that of an available light pipe, while preserving throughput. Clearly, there is an advantage to using a larger light pipe, since, in matching the beam diameter to the light pipe diameter, the divergence angle is automatically reduced.

The diameter of the light pipe may, for example, be 32 mm, as mentioned in the following paragraph. It is considered feasible to use a smaller diameter light pipe, e.g., 16 mm, but it would not usually be desirable to use a diameter substantially below 16 mm. As pointed out in copending application Ser. No. 07/487,601, the light absorbance per meter, for beams having diameters 32 mm, 16 mm, and 8 mm, is inversely proportional to the diameter (except at 0° grazing angle). As further pointed out in the copending application, since the absorbance is doubled from 32 mm to 16 mm, and quadrupled from 32 mm to 8 mm, a substantial penalty is paid for using too small a light pipe diameter.

FIG. 8 also illustrates the advantage of having the smallest possible detector 110, i.e., the lowest value of r. It can be seen that the use of a small area detector can be advantageous, since this will limit the divergence angle for a given size light guide. Consider the following example: Assume a convenient light guide diameter $d_2$ of 32 mm, a detector lens diameter $d_1$ matching that diameter, a focal length $f_1$ of 20 mm, and a detector radius r of 0.5 mm For this case, the maximum divergence in the light guide will be 1.43 degrees; and the median ray divergence will be approximately 1 degree. If the detector radius r is reduced to 0.25 mm, the maximum ray divergence will be 0.71 degrees and the median ray divergence will be about 0.5 degrees. This difference can be particularly significant when attention is directed to the affect which the choice of coating material for the light pipe reflecting surface has on the angle of minimum reflectance.

Applicant has obtained surprising results from comparisons of locations of the point of lowest total reflectance of various potential reflective coating materials. A material which has very high reflectance values, at normal incidence such as aluminum, may be a less desirable light pipe coating than a material having lower reflectance values at normal incidence but a larger acceptable grazing angle, such as nickel. Because a larger acceptable grazing angle of the coating will tolerate larger divergence angles of the rays in the radiation beam, significant throughput improvements (reduced absorbance losses) are obtainable.

Figure 9:
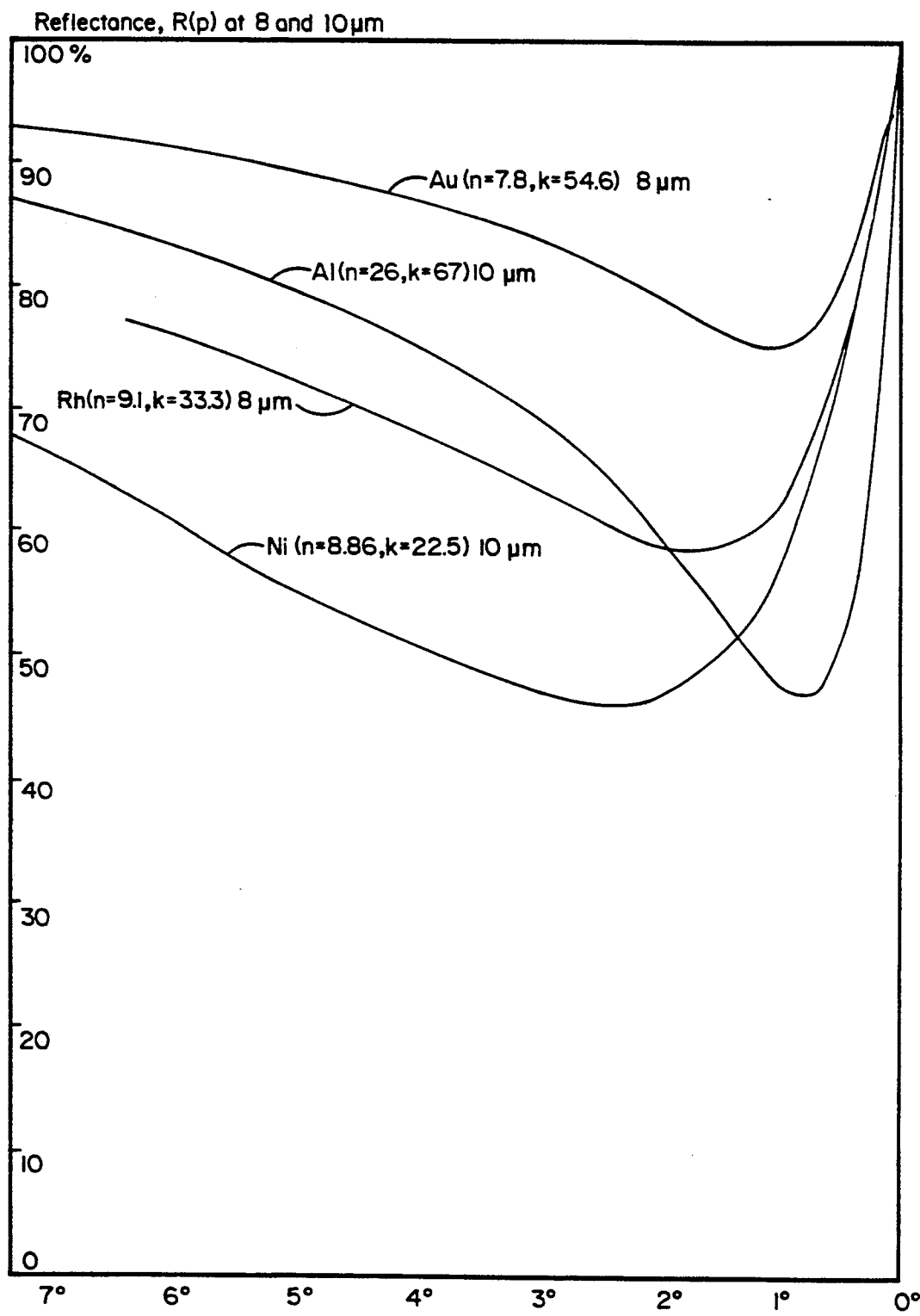

FIG. 9, which corresponds to FIG. 6 in the related application, compares the reflectance of four metals—gold, aluminum, rhodium, and nickel—at angles near grazing incidence. These metals share the characteristic of being relatively immune to degradation with time, compared to other materials that might be used in light pipes. It is clear from this figure that gold would be an excellent material for the light guide coatings. However, it is both very expensive and difficult to apply as a coating on the inside of long tubes.

Comparing the four curves of FIG. 9, it can be seen that the ideal light guide optical material would be one with a high value of "k" and a low value of "n". The "n" and "k" values represent the "real" and "imaginary" parts, respectively, of the index of refraction of a given material. Aluminum, for example, with high values of both "k" and "n", is a good reflector for angles far from grazing, but a poor reflector for angles near grazing. This is due to the fact that a high value of "n" gives rise to a reflectance dip which is both quite deep and located very close to grazing incidence.

Rhodium and nickel are only fair reflectors at angles near normal incidence, due to their low values of "k". However, both of these materials have relatively low values of "n", with the result that the dip in their reflectance is displaced away from grazing. Therefore, they are both considerably better reflectors than aluminum at angles very near grazing. In addition, nickel is inexpensive and can be easily coated on the inside of metallic tubing. These are important factors for light pipes of desirable lengths, e.g., in the range of five to ten feet.

It is apparent from FIG. 9 that, once the grazing angle of the radiation in the light pipe is less than the value for minimum reflectance (the lowest point in each curve), the reflectance will increase dramatically for further reductions in angle. Therefore, to the extent that the angle of divergence of radiation in the pipe is below the grazing angle at which minimum reflectance occurs, the throughput will be disproportionately improved.

As stated above, the practicability of light pipes for collimated radiation beams, which applicant has demonstrated and enhanced, permits a radically new and improved gas cell design.

From the foregoing description, it will be apparent that the apparatus and method disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. A gas analyzing FTIUR spectrometer system comprising:
    a gas cell providing a long flow path for the gas being analyzed, said gas cell being a hollow radiation-guiding light pipe which has a highly reflective cylindrical inner surface, and whose cross-sectional area remains substantially constant from its radiation inlet end to its radiation outlet end;
    means including an FTIR interferometer for directing a collimated IR radiation beam through the gas cell;
    said collimated beam having a cross-sectional area in the gas cell flow path sufficient to fill the cross-sectional area of the hollow gas cell light pipe;
    said gas cell light pipe having a sufficiently large cross-sectional area to permit said collimated beam to pass through the length of the gas cell with minimized loss of radiation transmission due to absorption of radiation by the cylindrical inner surface of the light pipe gas cell;
    a detector which receives radiation which has passed through the gas cell;
    a gas entry port at one end of the gas cell light pipe; and
    a gas exit port at the other end of the gas cell light pipe.

2. The gas analyzing system of claim 1 which comprises:
    a plurality of parallel tubes which provide the length of hollow gas cell light pipe; and
    a plurality of roof-top reflectors which reverse the direction of the collimated radiation beam and transfer it from one tube to the next tube.

3. The gas analyzing system of claim 1 in which the ratio of the length of the hollow gas cell light pipe to its diameter is at least 25.

4. The gas analyzing system of claim 1, which also comprises
    optical elements external to the hollow gas cell light pipe so arranged as to reduce the angular divergence of the collimated radiation to the lowest value consistent with the required radiation throughput of the system.

5. The gas analyzing system of claim 4 in which the angular divergence of the collimated radiation is such that the median ray divergence is no greater than approximately 1° from the axis of the hollow gas cell light pipe.

6. The gas analyzing system of claim 4 which comprises:
    coating material on the inner surface of the gas cell light pipe whose point of minimum reflectance occurs at a grazing angle larger than the median angular divergence of the collimated radiation.

7. The gas analyzing system of claim 4 which comprises:
    coating material on the inner surface of the gas cell light pipe whose point of minimum reflectance occurs at a grazing angle larger than most of the angular divergence of the collimated radiation.

8. The gas analyzing system of claim 1 which comprises:
    coating material on the inner surface of the gas cell light pipe whose point of minimum reflectance occurs at a grazing angle larger than 1°.

9. The gas analyzing system of claim 8 in which the coating material is nickel.

10. The gas analyzing system of claim 1 in which the diameter of the gas cell light pipe is at least approximately 16 millimeters.

11. The gas analyzing system of claim 1 in which the length of the gas cell light pipe is at least 40 centimeters.

12. The gas analyzing system of claim 10 in which the length of the gas cell light pipe is at least 40 centimeters.

13. The gas analyzing system of claim 1 which also comprises:
    means separate from the gas cell light pipe for condensing or expanding the size of the collimated IR radiation beam.

14. A method, for spectroscopic analysis of a gas sample in a system having a pre-sample infrared radiation source and a post sample infrared radiation detector, comprising:
    outputting a collimated interferometer beam from the pre-sample radiation source;
    filling the passageway of a hollow light pipe system with a gas sample to be analyzed; and
    directing the collimated beam of infrared analytical radiation through the hollow light pipe system on its way from the source to the detector, the cross-sectional area of the beam filling the hollow light pipe and being confined by the hollow light pipe.

15. The method of claim 14 in which the hollow light pipe passageway and the collimated beam are both cylindrical.

16. The method of claim 15 which also comprises:
    reversing the paths of both the gas sample and the radiation in the hollow light pipe system so that the total system length is provided by a compact arrangement of parallel pipe units.

17. The method of claim 16 in which the radiation path is reversed by a rooftop mirror at each pipe-to-pipe connection.

18. The method of claim 14 in which the gas sample is forced continuously through the hollow light pipe system.

19. The method of claim 14 in which:
    a volume of gas is trapped in the hollow light pipe system as a sample during analysis; and
    the hollow light pipe system is subsequently purged by forcing through the pipe system a volume of purging gas not substantially greater than the volume of the trapped sample.

20. The method of claim 14 in which the gas and the radiation enter the pipe system at its inlet end and exit the pipe system at its outlet end.

* * * * *